United States Patent
Banks et al.

(10) Patent No.: US 9,134,238 B2
(45) Date of Patent: *Sep. 15, 2015

(54) METHOD FOR DETERMINATION OF SYSTEM PARAMETERS FOR REDUCING CRUDE UNIT CORROSION

(75) Inventors: Rodney H. Banks, Aurora, IL (US); Steven R. Ciota, Downers Grove, IL (US); Sascha J. Welz, Chicago, IL (US)

(73) Assignee: NALCO COMPANY, Naperville, IL (US)

(*) Notice: Subject to any disclaimer, the term of this patent is extended or adjusted under 35 U.S.C. 154(b) by 626 days.

This patent is subject to a terminal disclaimer.

(21) Appl. No.: 12/957,854

(22) Filed: Dec. 1, 2010

(65) Prior Publication Data

US 2012/0142113 A1 Jun. 7, 2012

(51) Int. Cl.
| | |
|---|---|
| *G01N 35/00* | (2006.01) |
| *G01N 33/20* | (2006.01) |
| *G01N 31/22* | (2006.01) |
| *G01N 31/02* | (2006.01) |
| *G01N 21/80* | (2006.01) |
| *G01N 21/83* | (2006.01) |
| *G01N 21/64* | (2006.01) |
| *G01N 35/08* | (2006.01) |
| *G01N 33/18* | (2006.01) |
| *G01N 21/05* | (2006.01) |
| *G01N 21/82* | (2006.01) |

(52) U.S. Cl.
CPC .............. *G01N 21/643* (2013.01); *G01N 21/80* (2013.01); *G01N 35/08* (2013.01); *G01N 21/05* (2013.01); *G01N 21/82* (2013.01); *G01N 31/22* (2013.01); *G01N 31/221* (2013.01); *G01N 33/1813* (2013.01); *G01N 2021/6421* (2013.01); *G01N 2021/6491* (2013.01); *Y10T 436/11* (2015.01); *Y10T 436/193333* (2015.01); *Y10T 436/25125* (2015.01)

(58) Field of Classification Search
None
See application file for complete search history.

(56) References Cited

U.S. PATENT DOCUMENTS

| | | |
|---|---|---|
| 4,355,072 A | 10/1982 | Mateika et al. |
| 4,379,848 A | 4/1983 | Yeaw |

(Continued)

OTHER PUBLICATIONS

Hoxter, G. "Suggested IsosbesticWavelength Calibration in Clinical Analyses," Clin. CHem. 25/1, 143-146 (1979).*

(Continued)

*Primary Examiner* — Yelena G Gakh
*Assistant Examiner* — Michelle Adams
(74) *Attorney, Agent, or Firm* — Benjamin Carlsen

(57) ABSTRACT

The invention provides a method and apparatus for determining the amount of various materials in a liquid sample. Because the apparatus is particularly resilient it can be used repeatedly with very harsh liquid samples such as boot water from an oil refinery. The apparatus uses at least one volume and/or concentration independent optical analysis method to determine at least one of: the pH, amount of chloride, and/or amount of iron in the sample. The optical property can be colorimetric, fluorescent or both and result from adding dyes, complexing agents, turbidity inducing compounds, and other optically effecting reagents to the sample. Because the measurements are concentration and volume independent they can be done continuously, quickly, and avoid the inconvenient start and stop procedures in prior art measurement regimens. The method further includes using a BDD cell to oxidize materials (such as sulfoxy compounds) that would otherwise interfere with the optical analysis and/or to sparge the sample with gas.

18 Claims, 11 Drawing Sheets

(56) References Cited

U.S. PATENT DOCUMENTS

| | | | |
|---|---|---|---|
| 4,548,708 | A | 10/1985 | Schwarzer et al. |
| 4,999,305 | A * | 3/1991 | Wolcott et al. .................. 436/52 |
| 5,094,958 | A | 3/1992 | Klainer et al. |
| 5,302,253 | A | 4/1994 | Lessard et al. |
| 5,324,665 | A | 6/1994 | Lessard |
| 5,326,482 | A | 7/1994 | Lessard et al. |
| 5,425,267 | A | 6/1995 | Herrmann et al. |
| 5,462,880 | A | 10/1995 | Kane et al. |
| 5,672,515 | A | 9/1997 | Furlong |
| 5,734,098 | A | 3/1998 | Kraus et al. |
| 8,088,097 | B2 | 1/2012 | Markle et al. |
| 2002/0000414 | A1 | 1/2002 | Kroll |
| 2004/0087031 | A1 * | 5/2004 | Simon, Jr. .................. 436/100 |
| 2007/0178595 | A1 | 8/2007 | Raghuraman et al. |
| 2009/0177143 | A1 * | 7/2009 | Markle et al. .................. 604/66 |
| 2010/0021958 | A1 | 1/2010 | Reed et al. |
| 2010/0108566 | A1 | 5/2010 | Scattergood et al. |

OTHER PUBLICATIONS

Biwersi, J., Tulk, B., Verkman, A. S., "Long-Wavelength Chloride-Sensitive Fluorescent Indicators," *Analytical Biochemistry*, vol. 219, 1994, pp. 139-143.

Chalk, S. J. & Tyson, J. F., "Determination of Chloride by Flow Injection Spectrophotometry with Membrane Reagent Injection," *Analytica Chimica Acta*, vol. 366, 1998, pp. 147-153.

Condiapure Water Disinfection Bulletin, Condias, GmbH, Germany, 2008.

Geddes, C. D., "Optical Halide Sensing Using Fluorescence Quenching: Theory, Simulations, and Applications—A Review," *Measurement Science and Technology*, vol. 12, 2001, R53-R88.

Haines, T. A., Akielasek, J. J., Norton, S. A., Davis, R. B., "Errors in pH Measurements in Low Alkalinity Waters," *Hydrobiologia*, vol. 107, 1983, pp. 57-61.

Hupert, M. et al., "Conductive Diamond Thin Films in Electrochemistry," *Diamond and Related Materials* vol. 12, 2003, pp. 1940-1949.

Koparal, A. S., Ün, U. T., Ögütveren, U. B., "Electrochemical Oxidation of Sulfite Ions in Aqueous Solutions," *Int. J. Environment and Pollution*, vol. 21, No. 6, 2004, pp. 579-587.

Lawrence, J., Robinson, K. L., Lawrence, N. S., "Electrochemical Determination of Sulfide at Various Carbon Substrates: A Comparative Study," *Analytical Sciences*, vol. 23, 2007, pp. 673-676.

Noiré, M. H. & Dureault, B., "Ferrous Ion Optical Sensor Based on Fluorescence Quenching," *Sensors and Actuators B*, vol. 29, 1995, pp. 386-391.

University of Washington, "NeSSI Gen II Specification," Center for Process Analytical Chemistry, 2004.

Urbano, E., Offenbacher, H., Wolfbeis, O. S., "Optical Sensor for Continuous Determination of Halides," AnalyticalChemistry, vol. 56, No. 3, 1984, pp. 427-429.

Waterston, K., Bejan, D., Bunce, N. J. "Electrochemical Oxidation of Sulfide at a Boron-Doped Diamond Anode," J. Applied Electrochemistry, vol. 37, 2006, pp. 367-373.

Zhelyaskov, V. R., Liu, S. Y., Broderick, M. P., "Analysis of Nanoliter Samples of Electrolytes Using a Flow-Through Microfluorometer," *Kidney International*, vol. 57, 2000, pp. 1764-1769.

* cited by examiner

US 9,134,238 B2

METHOD FOR DETERMINATION OF SYSTEM PARAMETERS FOR REDUCING CRUDE UNIT CORROSION

CROSS-REFERENCE TO RELATED APPLICATIONS

Not Applicable.

STATE REGARDING FEDERALLY SPONSORED RESEARCH OR DEVELOPMENT

Not Applicable.

BACKGROUND OF THE INVENTION

This invention relates generally to methods of reducing corrosion in a crude unit. More specifically, the invention relates to methods of optimizing system parameters in a process stream of a crude unit to reduce corrosion in the crude unit. The invention has particular relevance to sampling dew point water and accumulator boot water to measure system parameters and respond to such measurements to reduce corrosion and/or corrosion byproduct deposition in the crude unit.

In a crude oil refinery, generally the oil is pumped from a storage tank to a crude unit for processing. The crude unit cleans the oil through water washing in a desalter and then splits the oil into fractions in an atmospheric distillation tower. These fractions are pumped to various processing units downstream of the crude unit (e.g., coker, catalytic cracker, hydrotreater etc.). Though corrosion and corrosion byproduct deposition (the latter sometimes referred to herein as fouling) occur in many areas of a crude unit, the most severe corrosion and fouling typically take place in the overhead condensing system of an atmospheric distillation tower system.

Refinery crude unit processing has becoming increasingly difficult in recent years and is predicted to become even more challenging and complex for several reasons. For example, significant increases in crude oil prices have caused refiners to aggressively pursue "opportunity" or "challenging" crudes that are obtainable at discounted prices. The lower price is linked to a crude property such as high acid or high solids content that makes it less desirable than the light, sweet benchmark crudes.

Refiners switch crude slates more frequently than in the past due to minimum on-hand crude oil inventory combined with increased crude oil variety. A crude slate switch typically upsets the steady state condition of a crude unit for up to several hours. Generally, about eighty percent of the corrosion and fouling occurs during these switches or disruptions, which normally last about twenty percent of the time. If fouling and corrosion issues are severe enough, the refiner will discontinue processing the crude oil or blend of crudes causing the problem. However, these challenging crudes are available to the refiner at a discount thus making them more profitable. Discontinuing such problematic crudes is accordingly not a very popular option.

In efforts to reduce corrosion, a crude unit may be serviced two or three times per week, or in some cases daily. Daily service at best provides a snap shot view of a dynamic crude unit system. Crude type and/or raw crude storage tanks are switched several times per week, sometimes daily. The contents of each tank are different from the others, so each switch causes a change of feed quality to the crude unit, many times upsetting the steady state status and causing disruptions in the system. Preheating, desalting, and distilling operations shift with the new crude, sending products and/or effluent water sources off specification. Many adjustments over several hours (in some cases days) normally take place to return the crude unit to steady state operation.

The most common current industry practice to control such disruptions and optimize crude unit operation is to provide enough manpower and man-hours. For instance, each crude unit may have an operating crew from three to ten people, depending on size and complexity of the unit. This crew may spend their day gathering various samples for wet chemistry lab testing, and measuring and making adjustments for temperature and flow to keep the unit running within specification. Such practice is typically geared towards keeping the unit operating properly with respect to fractionation quality cut points and end points, with minimal attention being paid to a specialty chemical corrosion control program. If a disruption is severe, changes may be made to the process chemicals and/or changes in levels, flows, or temperatures may be recommended around the crude unit to keep the dynamic system in as optimum a condition as possible.

Attempts to compensate for periodic or sometimes prolonged lack of human involvement include installing online pH meters on atmospheric distillation towers overhead accumulator water boots; however, due to a high rate of fouling of the pH sensor only a small percentage of these meters operate correctly for any length of time. Online instrumentation, such as pH meters, requires routine maintenance and calibration. Moreover, online pH merely tracks the pH and sends an alarm to the operator when the pH is outside the control limits. Often, poorly calibrated and/or fouled pH meters cause frequent alarms. This frequency tends to minimize the effectiveness of the alarm system. Due to the lack of industry success with online pH metering and other monitoring efforts refiners have not pursued more exotic and effective online instrumentation for process chemical programs. There thus exists an ongoing need for more sophisticated and effective online and/or automatic methods for monitoring parameters and reducing corrosion in crude units.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

BRIEF SUMMARY OF THE INVENTION

At least one embodiment of the invention is directed towards a method of measuring at least one property of a predominantly liquid sample. The method comprises the steps of: 1) adding at least one chemical reagent to the sample, the chemical reagent capable of inducing a measurable optical effect when added to the sample that is directly related to the property to be detected, 2) measuring the optical effect, and 3) deducing the value of the property by comparing the measured optical effect to pre-determined values associated with the property to be determined. The relationship between the measured optical effect and the property to be determined is independent of the volume of the liquid sample and independent of the volume of the reagent added to the sample.

The measured property may be one item selected from the list consisting of: pH, iron concentration, chloride concentration, and any combination thereof. The measured optical effect may be a colorimetric effect, turbidity effect, or a fluorescent effect. The reagent may be thoroughly mixed with the sample. The optical effect may be measured by determining an absorbance level at a particular wavelength whose measurement is recognized as an isosbestic point for all values of the property, detecting at least one other absorbance level for one other wavelength, comparing the two absorbance levels with pre-determined data, and correlating the two absorbance levels to the known absorbance levels of a particular value of the property. The reagents may be selected from the list consisting of: bromcresol purple, fluorescein, PTSA, TPPTSA, calcein blue, Ferrozine, silver nitrate, thioglycolic acid, ammonia, pH buffer, ferric iron reductant, fluorescent dye, lucigenin, and any combination thereof.

The optical effect may be measured by the reagents being at least two fluorescent dyes, one of the dyes' fluorescence at a first wavelength is affected by the value of the property and one of the other dyes' fluorescence at a second wavelength is unaffected by the value of the property. The method may further comprise the steps of measuring the ratio of the fluorescence intensities of the first and second wavelengths in the sample, comparing that ratio to the ratio of the fluorescence of the first and second wavelengths in a control having a known value of that property, and correlating the proportional change in the two ratios to the property value. The optical effect may be measured by the reagent's absorbance and fluorescence where the absorbance is unaffected by the value of the property and the fluorescence is affected by the value of the property, by comparing the ratio of the fluorescence to absorbance to a control having a known value of the property, and correlating the proportional change in the two ratios to the property. The reagent may form a complex with a compound that causes the property, the absorbance of the complex at a pre-determined wavelength is directly related to the amount of that compound present and not to the amount of reagent added.

The sample may be positioned within an apparatus. The apparatus comprises at least one reagent source constructed and arranged to feed the reagent into a chamber where it is mixed with the sample and the sample is moved past an optical sensor that measures the optical property. The apparatus may further comprise a light source which may be positioned in line or perpendicular to the optical sensor. The light source may also be in line or perpendicular to a BDD cell through which the sample passes before the reagents are added. The BDD cell may be constructed and arranged to oxidize sulfoxy compounds. The light source may also be in line or perpendicular to a vertically angled sensor flow path through which the sample flows whereby measured light passing to the optical sensor passes horizontally through the sample. There may be at least two optical sensors and the sensors are positioned along a horizontal plane relative to the vertical flow path. The apparatus may further comprise a tube downstream from the sensor, at least a portion of the tube is higher than the sensor and is horizontally angled, the tube is constructed and arranged to facilitate the migration of gas bubbles away from the sensor. The tube may be inverted U-shaped. The apparatus may further comprise a gas source upstream from the sensor, the gas source constructed and arranged to sparge undesired materials away from the sample. The apparatus may be interfaced with a control system governing at least some of the operations of a chemical process stream from which the sample was taken, the measured data resulting in the control system implementing a counter-measure in response to the property.

BRIEF DESCRIPTION OF THE DRAWINGS

A detailed description of the invention is hereafter described with specific reference being made to the drawings in which.

DETAILED DESCRIPTION OF THE INVENTION

Figure 1:
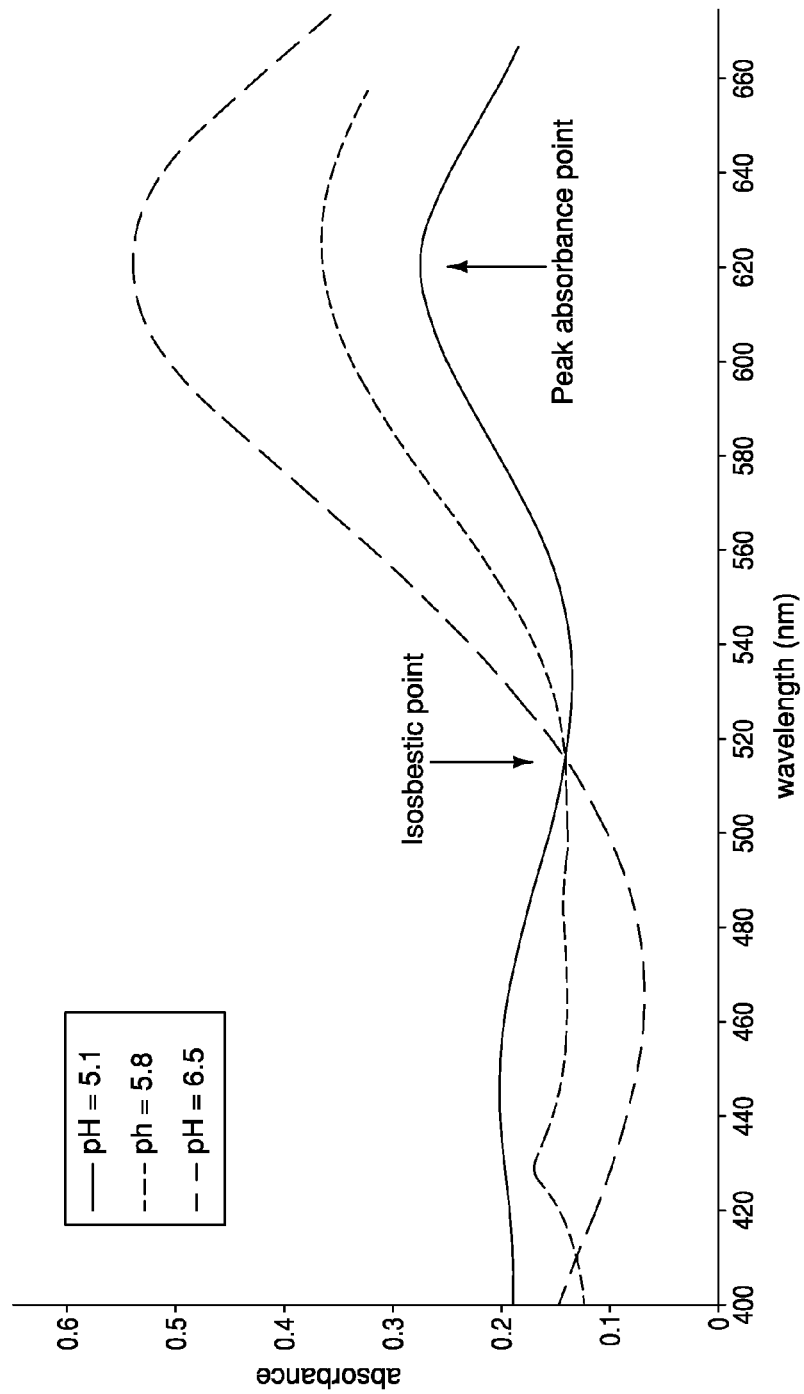
FIG. 1 is a graph used to show how the isosbestic point can be used to determine parameters of a liquid sample.

For purposes of this application the definition of these terms is as follows:

"BDD electrode" means an electrode that is at least partially covered with p-type diamond material in which at some of the covalent bond sites where carbon atoms would be in a pure diamond material there are boron atoms covalently bonded instead. The BDD electrode is used in an electrochemical cell in which the BDD electrode is the anode.

"Blank sample" means a liquid sample not containing reagent

"Boot Waters" means a liquid sample taken from the aqueous phase of a distilled fraction of oil, in which the fraction has condensed and separated into an aqueous phase and an organic phase and are commonly (but not necessarily) collected from an accumulator downstream from a heat exchanger.

"Colorimeter" means a device, which measures the intensity of transmitted light at a particular wavelength that passes through a sample.

"Controller" means a manual operator or an electronic device having components such as a processor, memory device, digital storage medium, cathode ray tube, liquid crystal display, plasma display, touch screen, or other monitor, and/or other components which is operable for integration with one or more application-specific integrated circuits, programs, computer-executable instructions or algorithms, one or more hard-wired devices, wireless devices, and/or one or more mechanical devices and which is operable to integrate the feedback, feed-forward, or predictive loop(s), and its functions may be at a central location, such as a network server, for communication over a local area network, wide area network, wireless network, internet connection, microwave link, infrared link, and the like, other components such as a signal conditioner or system monitor may be included to facilitate signal transmission and signal-processing algorithms.

"Dew Point Water" means a liquid sample taken at the point of initial condensation of steam to water or the temperature at which a phase of liquid water separates from the water vapors and liquid hydrocarbons and begins to form liquid water as the vapors cool. This sample may be formed in collectors that are cooled by coils containing cooling water that is circulated through them. Dew point water will contain the highest amount of HCl and other acids relative to water samples taken further downstream.

"Ferrozine" means a mixture of 3-(2-pyridyl)-5,6-bis(4-phenylsulfonic acid)-1,2, 4-triazine, monosodium salt and ammonium thioglycolate.

"Fluorometer" means a device, which measures the intensity of light that is generated by a sample as it fluoresces that has a different wavelength than the light projected into the sample. The fluorescence light can be measured at an angle (which can be 90°) with respect to the light projected into the sample.

"Interface" means the solid, electromagnetic, optical, virtual, or other interconnection between the analyzer and at least one other item through which electricity, plasma, light, radiation, fluid, data, information, matter, reagent, waste, material to be sampled, energy, heat, liquid, and/or gas pass between the analyzer and the item.

"PTSA" means Pyrene tetrasulfonic acid.

"Sparging" means introducing gas into a liquid for the purpose of creating a plurality of bubbles that migrate up the liquid and remove a particular material from the liquid through contact between the bubbles and the particular material.

"Sweeten" means to remove or render non-reactive a particular unwanted composition present in an aqueous fraction, including but not limited to hydrogen sulfide and other sulfur based compounds.

"TPPTSA" means 5,10,15,20-tetraphenyl-21H,23H-porphine-tetrasulfonic acid, tetrasodium hydrate.

"Turbidity Meter" or "Turbidimeter" means a device, which measures the intensity of light within a liquid that is scattered from a source beam of light as a result of the source beam of light interacting with particles within the liquid. The wavelength of the scattered light is the same as that projected into the sample.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Othmer Encyclopedia of Chemical Technology*, 5th Edition, (2005), (Published by Wiley, John & Sons, Inc.) this definition shall control how the term is to be defined in the claims.

Embodiments of the invention include a method of analyzing and an apparatus for analyzing properties and contents of a water sample. The water sample can be from crude unit overhead condensers. The analysis may be used to control a chemical corrosion control system.

At least one embodiment of the invention is directed towards a method of measuring system parameters for control of product feed in a crude oil refinery. At least one embodiment is directed to a method of reducing corrosion in a crude oil refinery by making use of the measured parameters. At least one embodiment is directed towards a heat exchanger operated in conjunction with at least one sensor capable of detecting the parameters. The parameters are one item selected from the list consisting of metal concentration, chloride concentration, pH, and any combination thereof. Metals contemplated by the invention for detection include but are not limited to: iron, copper, molybdenum, nickel and zinc. In at least one embodiment, one or more of the parameters are measured by an analyzer, which has at least one sensor.

Measuring the properties and compositions of various condensed water fractions can be complicated. The fractions that are analyzed typically are a widely diverse (and at least partially) and aqueous compositions comprising water, light hydrocarbons, hydrogen sulfide, and suspended solids of iron sulfides and iron oxides which can be agglomerated with heavier organics, amines, ammonia, organic acid (such as acetic acid) and silica. The fractions typically vary in pH, chloride concentration, and iron concentration and knowledge of these values is important in proper facility operation. If pH is too low, corrosion of downstream equipment can occur. Excess chloride is an indicator that excessive corrosive hydrochloric acid is present. Excess iron is indicative of steel corrosion and reacts with sulfides to form FeS particles that deposit on internal system surfaces. Of particular use is determining the parameter values early in the condensation region to allow adequate time to properly enact a corrosion control program such as strategically injecting neutralizing amines (for pH control), filming inhibitors (for iron control), caustic solutions (for HCl control), and the like.

Performing these measurements however is quite a challenge as the compositions of the fractions are harmful to most sensors. In prior art sensors, small diameter plastic tubing, peristaltic pumps, valves and other mechanical parts rapidly become fouled and/or plugged. Particles, oils, and other organics cause drift in baselines and calibration errors in optical components. Colorimetric equipment in particular can become inaccurate due to background color, turbidity interference, and fouling of optical surfaces. Electrochemical devices and especially ion selective electrodes can be disturbed by sulfide compounds, which are often present in amounts exceeding hundreds of ppm.

Ideally the parameters would be determined when or before the fractions enter the heat exchangers and/or at or before the dew point of steam. The value of the parameters collected at the dew point provides the most accurate prediction of what degree and form of downstream corrosion will ultimately occur and allows for precise use of a corrosion control program and would maximize the lifespan of the heat exchangers.

Unfortunately, practically no dew point samples are normally available. As a result common practice is to instead obtain measurements on boot waters where the water in the fraction has completely condensed and to use that measurement to control chemical dosage and the need for a corrosion control program. Dew point samples may be obtained according to the disclosures of U.S. Pat. Nos. 4,355,072 and 5,425,267 and U.S. patent application Ser. No. 12/263904.

Prior art methods of measuring parameters such as pH, chloride and iron with colorimetry are reagent based. They involve adding a known amount of reagent to a set volume of sample. This has a number of disadvantages. First if there is an error in adding the correct amount of reagent, the reading will be incorrect since the absorbance measured depends on the amount of reagent. Second it is cumbersome because a specific volume of sample must be removed from a dynamic system. For accurate results, a start-stop process is normally used. This process consists of acquiring a sample and metering a known volume of it into a vessel. Then a known amount of reagent is added and mixed. A far better system would involve measuring a parameter by adding a small volume of reagent into a flowing sample without needing to control the amount of reagent. In such a system, as the added reagent disperses in the flowing sample, its concentration continuously decreases. Therefore, prior art methods would give errors since the measured absorbance depends on the now unknown amount of reagent in the sample. This can be overcome by referencing the amount of sample by a value that relates to the volume of reagent in the sample or reagent concentration in the sample.

In at least one embodiment a parameter is measured directly by adding an amount of a reagent to a liquid sample of a refinery process stream and directly measuring an optical property directly related to that amount of reagent wherein the measured parameter is not dependent on knowing the concentration of the reagents in the liquid sample. In at least one embodiment the measured parameter is one item selected from the list consisting of: pH, iron (or other metal) concentration, and chloride concentration.

In at least one embodiment the pH is directly measured by using the isosbestic point of a colorimetric dye. FIG. 1 illustrates a graph of the absorbance vs. wavelength of the same concentration of a colorimetric dye in samples having various pH values. While each of the different pH samples has a unique absorbance at the pH wavelength, they all share a single wavelength at which the colorimetric dye displays a constant absorbance level regardless of pH, the isosbestic point. By ratioing the absorbance at the pH wavelength to that at the isosbestic point, the pH value obtained is independent of the relative amount of reagent or sample. In the prior art an algorithm is used which relies upon knowing the sample volume and the maximum absorbance wavelength to determine the pH.

In the invention however rather than simply using the maximum absorbance to determine pH, pH is instead determined by ratioing the maximum absorbance to the isosbestic point. The isosbestic point for the specific colorimetric dye used is a pre-determined characteristic of the dye that depends only on its concentration. Moreover for that dye, the maximum absorbance is also known for various pH values. As a result, once colorimetric readings are taken for a sample, if the isosbestic and the maximum absorbances are known, and the readings confirm the pre-determined isosbestic point, then the readings can be identified as corresponding to the graph of a specific pH and the pH for the sample can be known without the need for knowing the reagent concentration. Initial blank sample measurements allow for accurate readings to be taken even for samples that are harder to measure with the prior art methods such as highly turbid or colored samples that interfere with the measured maximum absorbance. Likewise blank sample measurements correct for accumulated fouling of the optic tube. Ratioing the maximum absorbance to the isosbestic absorbance cancels out the effects of light source intensity variation and detector responsiveness variation. In at least one embodiment effects that are additive such as color, turbidity, and tube fouling are corrected by blank subtraction.

In at least one embodiment effects that are proportional such as light intensity and detector sensitivity are corrected by ratioing.

Figure 2:
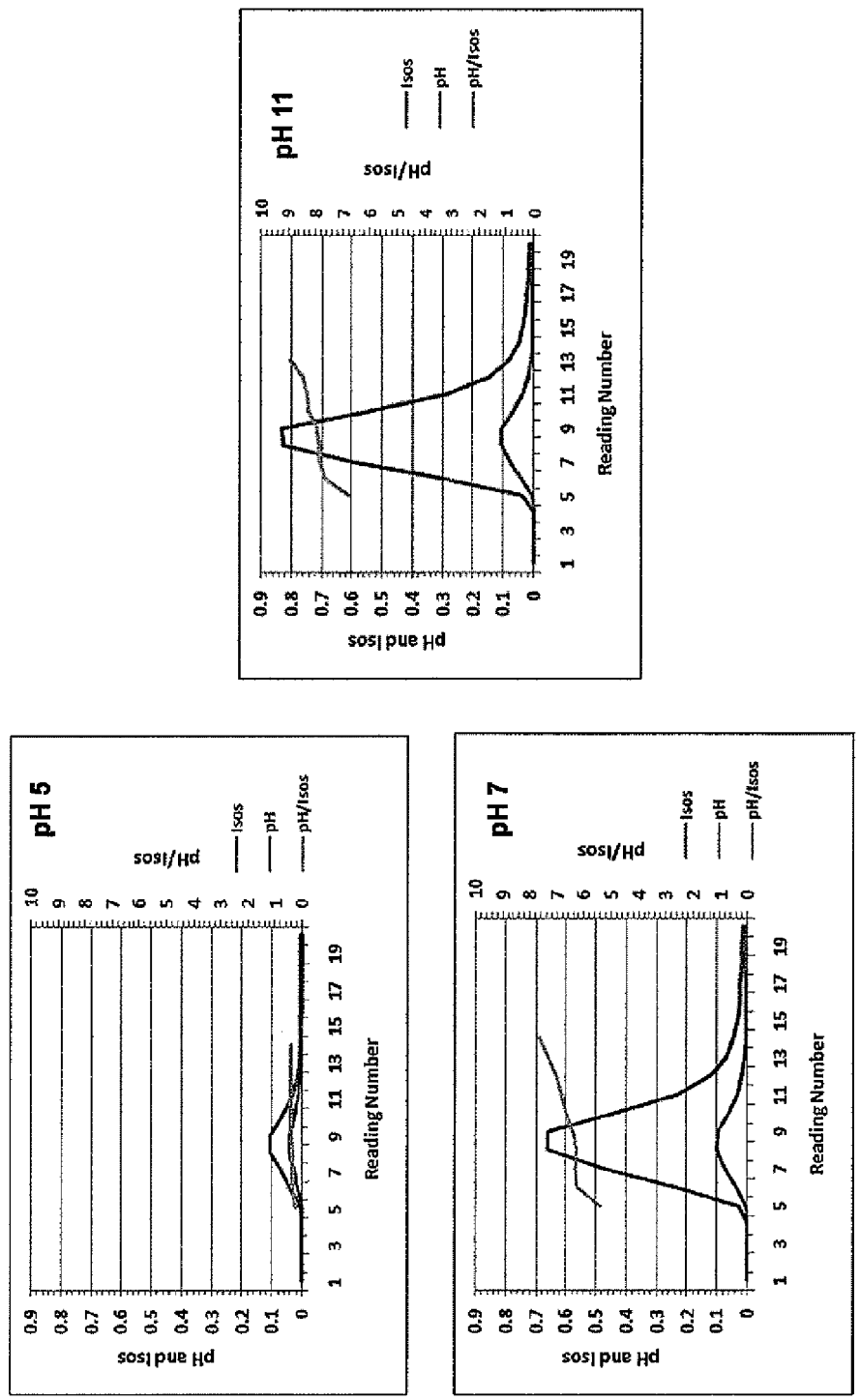
FIG. 2 contains graphs used to illustrate how isosbestic points at different pH can be used to determine parameters of a liquid sample. In these graphs the left Y-axis is absorbance for Isosbestic points and pH channels. The right Y-axis is the ratio pH/Isos.

In at least one embodiment, optical readings are performed on a number of pump push strokes for a number of measurements while the reacted sample flows through the colorimeter. Data arrays are filled with all transmittance data for the isosbestic point and pH band. The reference photodiodes for both LEDs are also read and are used to correct for any variation in light source emission intensity variation. Representative data for three runs on calibration standards are plotted in FIG. 2 where the left axes are absorbance for the two channels. The isosbestic curves illustrate how the pH dye concentration increases to a peak and then declines back to the baseline. Since the runs are identical in function, the isosbestic curves are seen to be the same while the pH curves increase at higher pH. The right axes are the calculated ratios of blank-corrected pH and isosbestic absorbances. The ratio curves (ph/Isos) should ideally be flat lines if the isosbestic correction is valid. It is seen that around the peak area they are horizontal. These plots clearly show the value of our technique of ratioing and how accurate values result. Readings could have been taken anywhere the ratio is constant within the desired error tolerance, not just at the peak, for example. In comparison, prior art methods, using the same range of readings, would have resulted in significant errors since the absorbance at only the pH wavelength varies widely.

The first four baseline points, or blank sample points, are averaged and stored. These exist as the sample liquid between the reagent injection point and optic tube flows through the optic tube. As the sample liquid continues to flow through the optic tube, sample mixed with reagent flows through the optic tube on which readings are taken. After all readings are collected, the arrays are searched for the peak in the isosbestic response. The corresponding peak in the pH curve is also extracted. The absorbances are calculated from the peak transmittances and the reference values as $\log_{10}$ (peak reference/peak transmittance) and are corrected for tube fouling and sample turbidity by subtracting the blank absorbances.

The ratio of corrected pH to corrected isosbestic absorbances is input to the calibration equation.

The pH calibration equation is according to the linear function:

$$pH = pK + pHSlope \times \log(Abs/(Abs_{11} - Abs))$$

Figure 3:
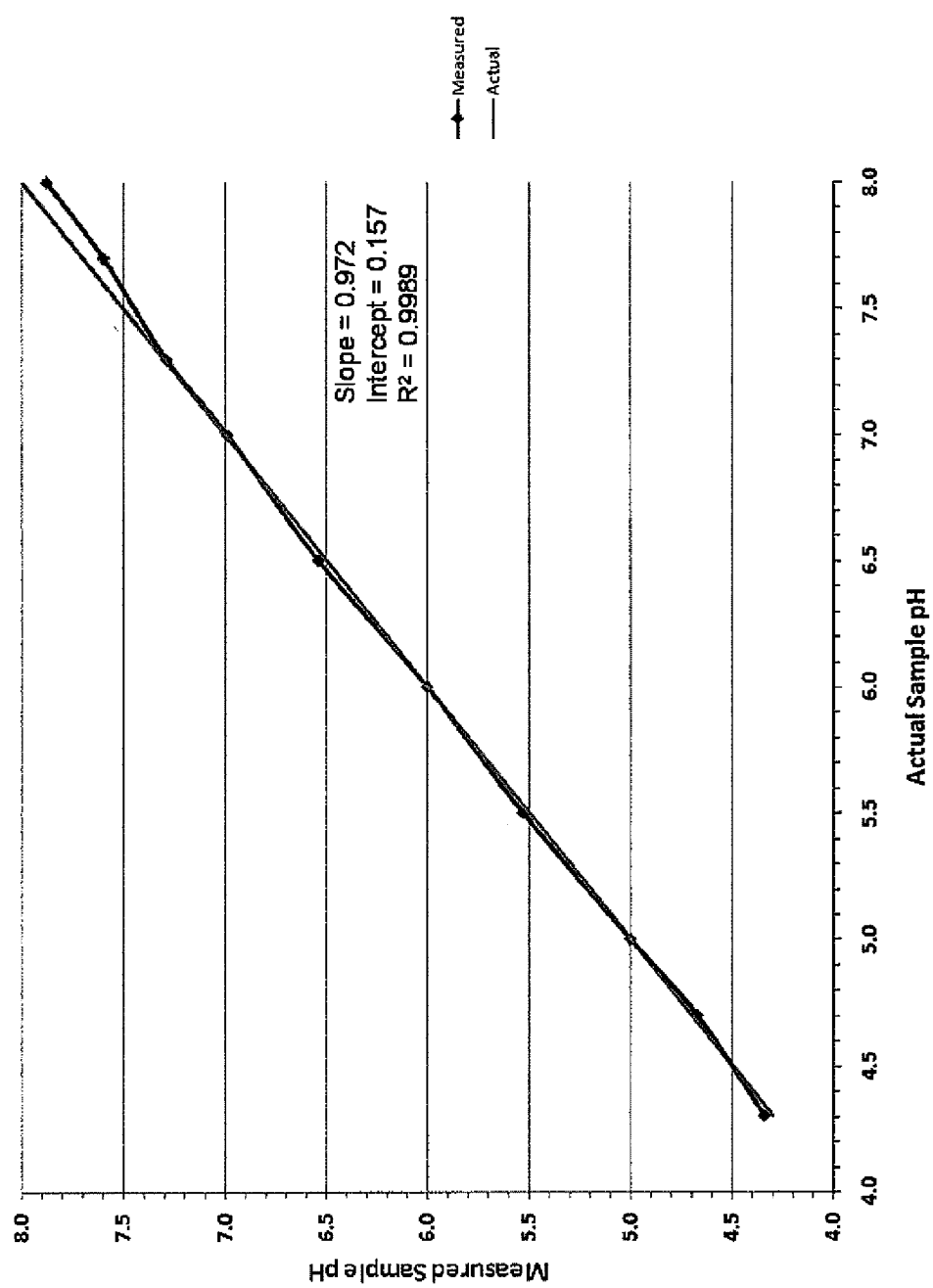
FIG. 3 is a graph used to illustrate the accuracy of the invention's measurements.

$Abs_{11}$ is the ratio for the pH 11 standard and is a constant in the equation representing the maximum absorbance at the pH wavelength. Using the other two pH standard ratios, pK and pHSlope are calculated as constants. When an unknown sample is measured, the ratio for the sample, Abs, is put into the equation and pH is found. FIG. 3 shows a typical calibration line and the equation used in calculating pH. Because the dye becomes less sensitive above pH 7.5, there is some inaccuracy in this area. In at least one embodiment a correction factor is used to correct for the inaccuracy above pH 7.5.

In at least one embodiment the colorimetric dye used is bromcresol purple. Bromcresol purple has an isosbestic point at 488 nm and maximum absorbance at 590 nm due to pH. As a result if samples are constantly taken from a refinery process stream, have bromcresol purple added to them, the pH can be accurately determined by ratioing the absorbance at 590 nm to that at 488 nm regardless of whether the sample volume or reagent concentration is known. As a result, it can be used to obtain accurate measurements without first determining or even knowing the volume of the reagent or having to compare the volume of the reagent to a control value. This allows for the analyzer to be a true online application where reagent dispersion in the flowing sample always gives accurate results. This is a significant improvement over the prior art that would only give accurate values when the reagent/sample volume ratio were known which cannot be known in a flowing sample stream. Thus the invention allows for the avoidance of the inefficient start-stop method used in the prior art.

In at least one embodiment parameters are measured directly using the ratio of the fluorescence of two fluorescent dyes. In the prior art fluorescent dyes have been used to measure the chloride content and pH of a sample by measuring the fluorescence of the dyes in the sample where the amount of dye and sample are both known. In at least one embodiment, two or more fluorescent dyes are added to a sample, each of which displays clear fluorescence at certain wavelengths. One dye's fluorescence intensity at a particular wavelength is directly dependent on the desired parameter and another dye's fluorescence intensity is completely independent of the desired parameter. The fluorescence intensity of the second dye is dependent only on its concentration in the sample mixture. By comparing the fluorescence ratio of the two dyes at the two wavelengths in a control sample where the parameter is known to the fluorescence ratio of an unknown sample, the parameter of the unknown sample can be determined.

In at least one of the embodiments the dyes used are lucigenin (9,9'-bis-N-methylacridinium nitrate) and PTSA to determine chloride concentration by fluorescence quenching. At 510 nm, lucigenin's fluorescence is dependent on chloride concentration while PTSA gives no fluorescence there. At 405 nm PTSA's fluorescence is independent of chloride concentration while lucigenin does not fluoresce there. By comparing the ratio of the fluorescence at 510 nm and 405 nm in a control to a measured sample, the parameters of the measured samples can be determined.

Figure 4:
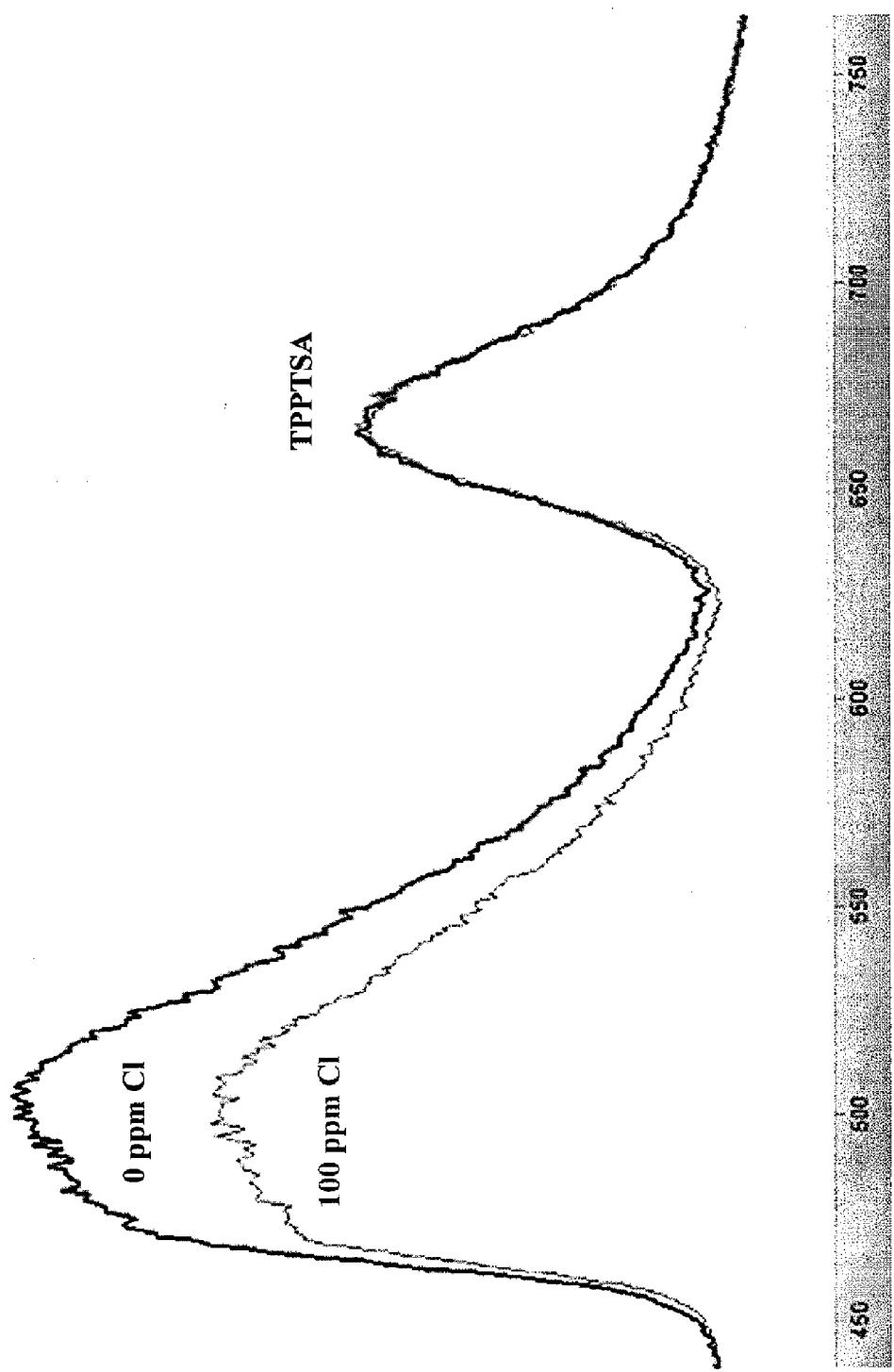
FIG. 4 is a graph used to illustrate how TPPTSA can determine chloride concentration using fluorescence ratioing. The Y-axis is fluorescence intensity.

Another suitable reference dye is TPPTSA which fluoresces at 670nm and whose fluorescence is independent of chloride concentration. By ratioing the fluorescence of lucigenin at 510um to the fluorescence of TPPTSA at 670um, the variation in dye concentration and sample volume is corrected. FIG. 4 illustrates the respective spectra for TPPTSA with and without chloride.

Figure 5:
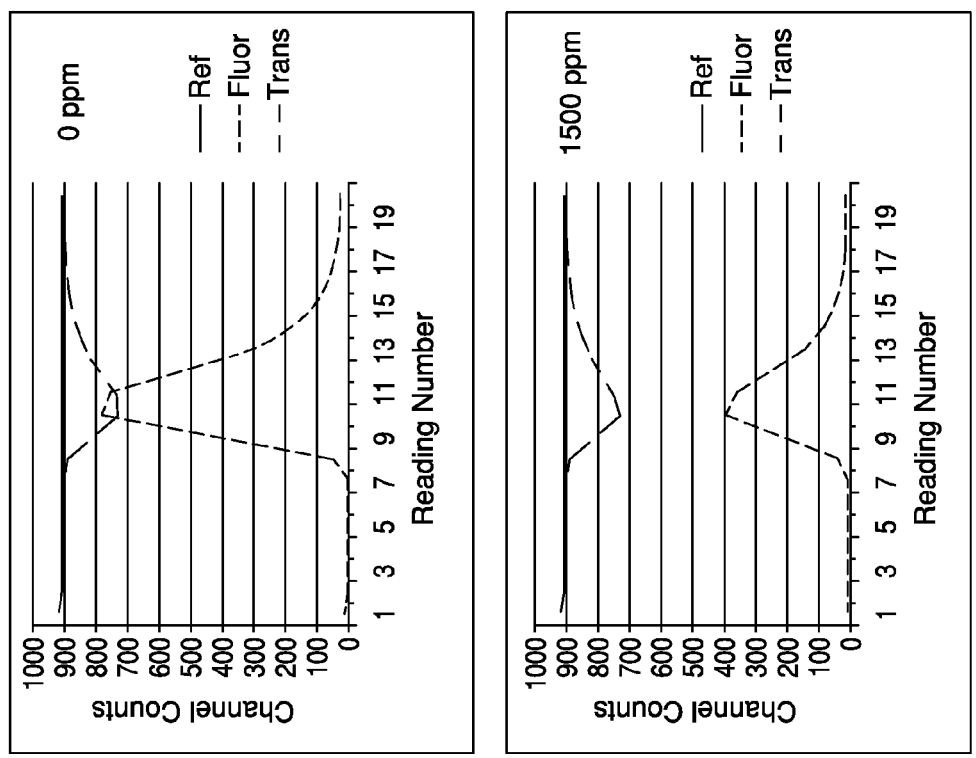
FIG. 5 is a graph used to illustrate how lucigenin fluorescence can be used to measure chloride using absorbance correction for sample and reagent volumes. In this graph Channel Counts is transmitted light intensity for the Trans curve. It is fluorescence intensity for the fluorescence curve. Absorbance of the lucigenin dye is calculated by log 10 (ref/trans).

In at least one embodiment the desired parameter content is directly determined by measuring florescence quenching using only one dye. In at least one embodiment the single fluorescent dye is a dye whose absorbance is diminished at a particular wavelength by dilution and whose fluorescence is diminished by the presence of a particular composition, for example by one containing chloride ions. As illustrated in FIG. 5, in at least one embodiment, this single dye is lucigenin whose absorbance at 433nm is dependent. only on its concentration, while at 510nm its fluorescence is dependent on the presence of chloride ions and its concentration. By ratioing its fluorescence to its absorbance, the effect of dilution or concentration of dye in the sample is canceled. The change in ratio between a control value and a measured sample can be used to determine the amount of chloride in a sample.

In at least one embodiment a colorimetric absorbance reading is taken of a complex formed between a parameter and an added reagent. A reagent is added that does not itself display colorimetric results at a given wavelength but if it forms a particular colored complex in the presence of a parameter, the presence of that complex will result in an apparent absorbance reading. In at least one embodiment, Ferrozine is added to a sample. At 560 nm Ferrozine itself does not appreciably display absorbance. If iron is present however, the Ferrozine complexes with the iron and shows absorbance at 560 nm which can be used to determine the exact amount of iron present. If the absorbance is read when an excess of Ferrozine is present, then the value for iron is accurate without knowing exactly how much Ferrozine or sample is present. In at least one embodiment a Ferrozine reagent buffer alters the background readings of the sensor and gives erroneous readings at 560 nm, so a second reading is taken at 690 nm where the Fe-Ferrozine complex does not absorb and the background reading at this wavelength is subtracted from that at 560 mn. The background level due to turbidity or color is removed from the reading.

In at least on embodiment silver nitrate is added to the sample. Silver nitrate does not appreciably absorb at 680 nm, but silver nitrate reacts with chloride to form silver chloride. Suspended silver chloride can be detected by measuring the absorbance at 680 nm from the path of a light beam passing through a sample. It can also be detected by measuring the turbidity in a turbidimeter at 680 nm. The measurement then does not depend on the level of silver nitrate concentration.

Figure 6:
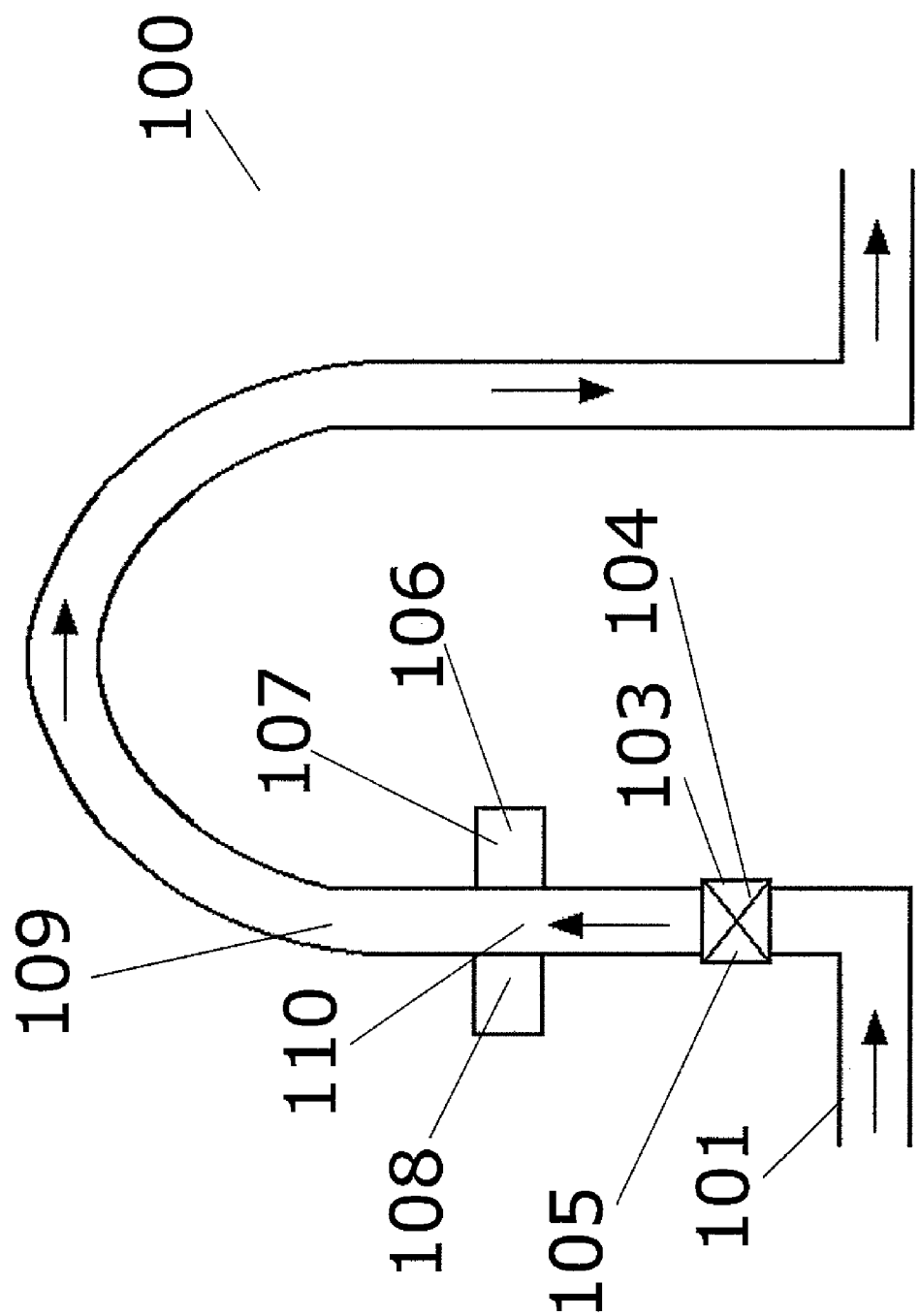
FIG. 6 is a side view illustration of an apparatus used to measure parameters of a liquid sample.

Referring now to FIG. 6 there is shown an apparatus (100) useful for determining parameters using colorimetric, turbidimetric, or fluorescence readings. The apparatus comprises a manifold (101) into which a liquid sample from a source is introduced. The liquid then can pass into a chamber (103) into which one or more reagent sources (104) are injected. The chamber includes a mixing device (105) which can be mechanical, flux based, ultrasonic, or based on any other known mixing technology in the art. In one embodiment, a reagent pump is connected to the chamber (103) by a capillary to minimize dead volume where diffusion of sample and reagent can occur. This avoids inaccuracies caused by a reagent injection that mostly comprises sample that had back-diffused into the reagent pump. In other embodiments the apparatus is constructed and arranged to avoid this problem with an elastomeric duck-bill or with other back-flow prevention devices known in the art.

After reagent addition, the liquid sample passes through a sensor tube path (110) along which is at least one colorimeter, turbidimeter, or fluorometric sensor (106). The colorimeter (106) comprises at least one optical sensor (107) and may also include at least one light source (108). The sensor (107) can be in-line and/or at an angle of more than zero and less than 180 degrees. In at least one embodiment the sensor (107) is located at a 90-degree angle to the light source (108). There optionally can be one optical sensor (107) located directly above the light source whose purpose is to read only the light output of the light source to reference colorimeter and fluorometer readings. Any variations due to aging or temperature changes can be corrected by ratioing to sensor (107) reading.

In at least one embodiment the light sources project and through-cell detectors view the sample in the same plane. In at least one embodiment this plane is perpendicular to the sensor tube path the sample is passing through. In at least one embodiment all of the sensors are perpendicular to the tube and are positioned at the same displacement along the tube so that the exact same sample volume is measured by all detectors simultaneously so they take the same "picture" of the sample flowing through the sensor tube.

Downstream and above the sensor (107) is an angled tube (109). The angled tube (109) comprises a portion of tube length that extends along a path that extends at a more horizontal angle than the more vertically angled sensor tube path (110). The positioning and shape of the sensor tube path (110) and angled tube path (109) facilitate the migration of gas bubbles up away from the colorimeter or fluorometer sensor (106). In at least one embodiment, sensor tube path (110) is substantially vertical. In at least one embodiment, at least a portion of the angled tube (109) is substantially horizontal. In at least one embodiment, as illustrated in FIG. 6 at least a portion of the angled tube (109) is an inverted U shape. In at least one embodiment, sensor readings are taken in synchronization to a sample pump such that the readings are taken when the pump is in its intake stroke where sample flow is momentarily stopped. This allows any bubbles to float out of the optical path so a true optical absorbance or fluorescence reading will be obtained.

Figure 7:
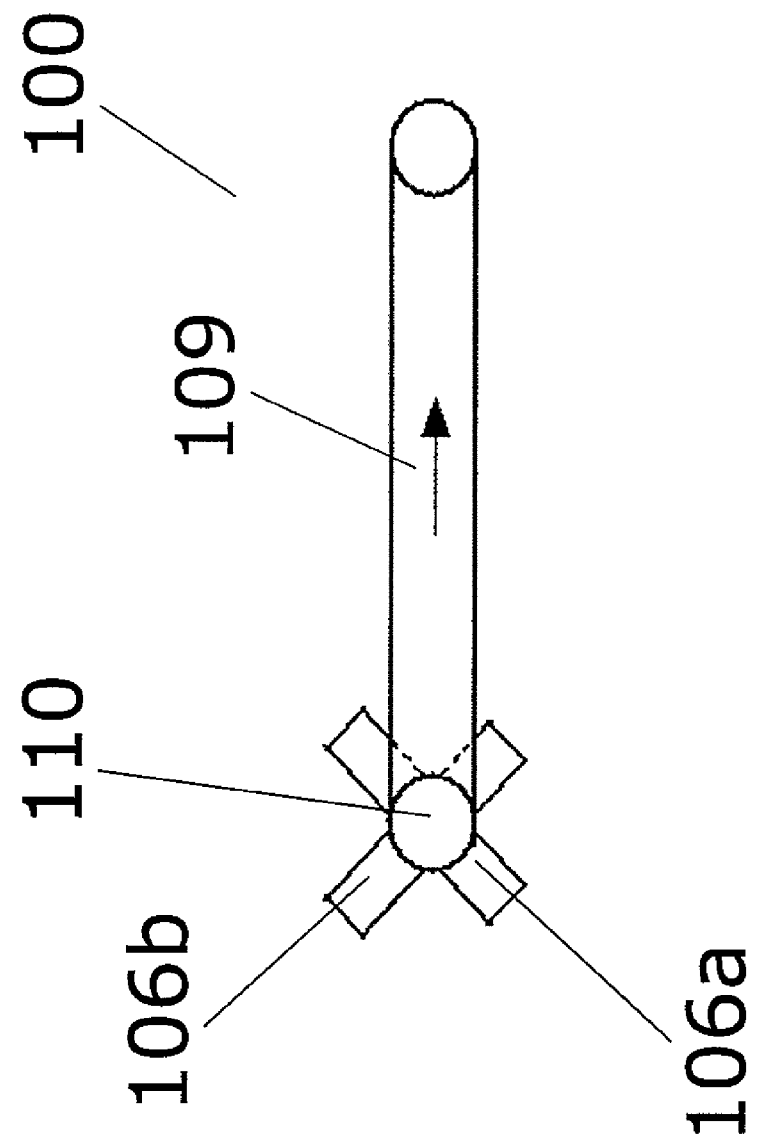
FIG. 7 is an overhead view illustration of an apparatus used to measure parameters of a liquid sample.

As illustrated in FIG. 7, in at least one embodiment the apparatus (100) comprises more than one sensor (106*a*, 106*b*). In at least one embodiment more than one of the sensors are planar relative to the sensor tube path (110). Planar sensors allow simultaneous measurements of more than one parameter. In at least one embodiment, the apparatus (100) can contain a temperature sensor, such as a thermistor, RTD, thermocouple, and the like, so temperature compensation of the absorbance or fluorescence readings can be performed.

In at least one embodiment after passing through the angled tube (109), the sample is either disposed of or is returned to the industry fluid stream it came from. Because the various sensors make parameter measurements that are independent of the volume of the sample, the apparatus can be constructed and arranged to continuously receive sample liquids and it can provide continuous measurements without constantly stopping liquid input to control for sample volume.

In at least one embodiment the apparatus comprises a mechanism to sparge the sample prior to its analysis by the sensor(s). Sparging facilitates the removal of materials from the sample that would otherwise impair, prevent, or otherwise complicate the sensor analysis. In at least one embodiment the sparging is accomplished by aerating the sample with air, nitrogen, or any other gas to remove materials that are volatile or to react the materials to the gas for the purpose of eliminating their adverse effects.

In at least one embodiment acid, such as nitric acid or in combination with an oxidizer, such as hydrogen peroxide are added to the sample prior to or during sparging to increase the rate of removal of volatile undesired material or react with the undesired material.

In at least one embodiment the sample passes through a filter to remove coarse particles before the sample is analyzed. The filter may have a pore size of between 10-200 micrometers. Flow or pressure sensors may also track the progress of the sample through the analyzer. In at least one embodiment the sample passes through a cooler or heater to make it compatible with the analyzer and reagent chemistries. In at least one embodiment the analyzer contains a cleaner reagent to remove fouling within the analyzer. Cleaner may be one or more organic amines such as ethanolamine or methoxypropylamine or an oxidizer such as hypochlorite or hydrogen peroxide. Cleaner can be introduced into the analyzer through a 3-way valve, pump, or by any other suitable mechanism.

In at least one embodiment at least one parameter is measured according to the methods and apparatuses disclosed in U.S. Pat. Nos. 5,326,482, 5,324,665, and 5,302,253. In at least one embodiment the analyzer comprises one item selected from the list consisting of a ceramic piston body, a solenoid pump (in the place of peristaltic pump), non-moving part turbulent flow mixers (in the place of coiled tube or static mixers). In at least one embodiment a leak detector is present. The leak detector can be a pressure sensor in the manifold (or other portion of the apparatus) or a conductivity sensor located under the manifold.

In at least one embodiment the apparatus comprises at least one of the monitoring sensors as disclosed in U.S. Pat. No. 5,734,098. In at least one embodiment the apparatus further comprises instruments to measure temperature, pressure, flow rate, and sample weight. In at least one embodiment the width of the sensor tube path (110) is optimal to maintain the mixing of the reagents with the sample. In at least one embodiment the mixing apparatus is constructed and arranged to mix the reagents with the sample in the same position that the sensor readings will be taken.

The apparatus can be dimensioned and its various components located and constructed such that it can be a modular component of an overall fluid process system. This allows for changes (such as installation, removal, maintenance, and/or upgrading) of just one element of the process system without requiring a modification of other portions of or of the entire system. In at least one embodiment at least some of the interfaces comprise elastomeric seals. In at least one embodiment the apparatus is engaged to a solid plate sized to fit a pre-established size on a wall or mount. In at least one embodiment the analyzer manifold and/or housing containing the analyzer itself is so sized. This allows the analyzer to be used as a "turnkey" or "peg-board" device as the term is understood in the art. In at least one embodiment, the manifold is constructed according to the standards for surface mount fluid distribution components according to the standards described in American National Standards, ANSI/ISA-76.00.02-2002, ISA (2002). In at least one embodiment one or more components of the apparatus (or the apparatus as a whole) are constructed and arranged out of one or more modular component connector substrate assembly systems as described in U.S. Pat. No. 7,178,556.

In at least one embodiment one or more ingredients of the sample are sweetened before the sample is analyzed by the sensor(s). Various sulfur-based compounds interfere with various analyses (and in particular colorimetric analyses). In at least one embodiment gas is sparged to remove $H_2S$ from the sample. In at least one embodiment the sparging gas is one selected from the list consisting of air, hydrogen, nitrogen, helium, and any combination thereof.

In at least one embodiment prior to a chloride analysis the sample is pre-conditioned to sweeten the sulfur bearing materials in the sample. Sulfur often exists in fractions in the form of sulfides and thiosulfates. While prior art methods teach sweetening sulfur oxides by reacting them with hydrogen ions to form hydrogen sulfite or hydrogen sulfate, their teachings regarding sweetening thiosulfate require reactions with hydrogen peroxide and boiling, such boiling reactions are impractical in an online analyzer context. Sulfur and thiosulfates in particular are particularly harmful as they poison silver used in chloride detection and ruin ion selective electrodes. In addition silver sulfide is insoluble and can plug or clog various components. Also some sulfides are non-volatile so sparging alone cannot remove them. The BDD cell is used to remove these non-volatile species.

In at least one embodiment the apparatus can perform real-time fractional analysis.

In an industrial process stream it is quite common for the composition of the stream to change over time due to various changes that occur in the system. This means that the liquid samples that pass through various locations at different times will have different properties. Because the apparatus can perform continuous analysis, the properties of each fraction can be continuously determined as they form.

Figure 8:
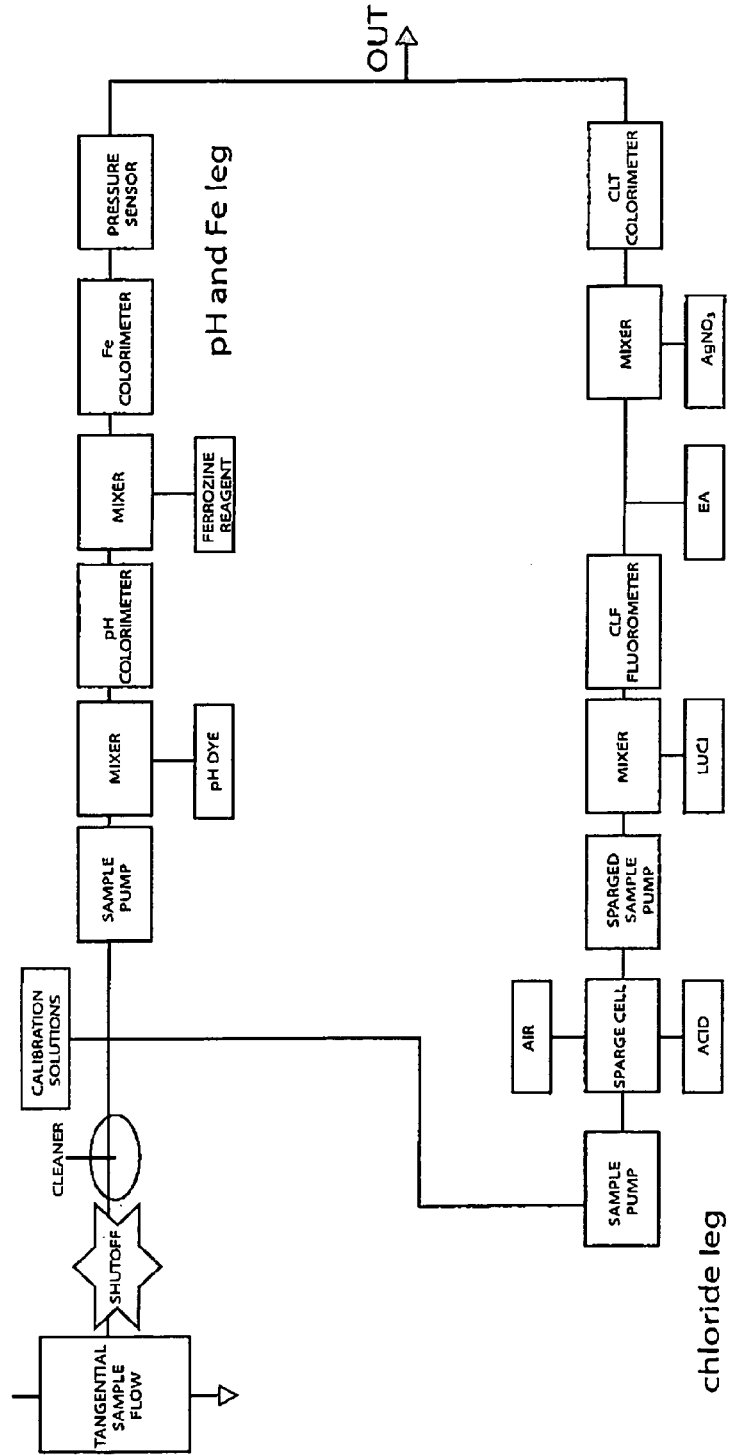
FIG. 8 is a flowchart illustration of various components in an apparatus used to measure parameters of a liquid sample.

Referring now to FIG. 8 there is shown a schematic representation of some components present in at least one inventive embodiment. The apparatus comprises a shut off valve through which a sample passes. A thermometer measures temperature and a coarse filter removes large particulate matter. A relief valve and pressure sensor are upstream or downstream of the colorimetric sensors. The flow and turbidity are also measured with appropriate equipment. A second fine filter further clarifies the sample before the colorimetric analysis. At least one sensor is used to measure each of pH, iron, and chloride. Each sensor corresponds to a reagent source, a regent pump, and a mixing chamber. A BDD cell can be upstream, downstream or both from the colorimetric sensors. A port is provided for injecting calibration solutions. In at least one embodiment the sample can be filtered through a tangential filter in addition to or instead of a coarse and fine filter. In at least one embodiment the apparatus is divided into two legs to segregate the two main, distinct chemistries (for example where one leg is sparged and the other is not.)

In at least one embodiment the apparatus comprises a BDD cell. Some sample ingredients, which are resistant to sparging and chemical sweetening, can instead be addressed with a BDD cell. For example sulfoxy compounds interfere with calorimetric analysis and are difficult to sparge or chemically sweeten. A BDD cell however oxidizes the sulfoxy compounds for example oxidizing thiosulfate into sulfate and thereby neutralizes the problems the sulfoxy compounds would otherwise cause. In at least one embodiment the BDD also imposes a uniform temperature within the sample regardless of the temperature of the sample when it is removed from the industrial process stream. In at least one embodiment the temperature of the sample is maintained at a temperature that is optimal for one or more of the analyses to be performed.

BDD electrode cells are particularly useful in this invention as they provide a large potential range without decomposing water, have a low capacitance background, are highly resistant to the harsh nature of the boot water sample, and are chemically inert and do not tend to adsorb sample constituents. The BDD electrode cell has a high over potential for gas formation, which allows for a very high and very effective voltage to be used to oxidize sulfur-bearing materials and generate hydroxyl radicals.

In at least one embodiment the BDD electrode cell is an anode and the cathode is an inert conductor. The cathode may be one item similar to and/or selected from the list consisting of: carbon, glassy carbon, platinum, stainless steel, hastelloy, and any combination thereof. In at least one embodiment the BDD electrode cell is within a lumen having an internal volume of between 5 and 100 ml. In at least one embodiment the apparatus comprises a module having a BDD electrode surrounded by a cathode mesh. In at least one embodiment nitric acid is added to the sample to increase its conductivity and enhance oxidation. In at least one embodiment the BDD electrode module contains a top hole for waste removal and gas venting.

In at least one embodiment the BDD electrode cell is used to generate various products including: hydroxyl radicals, ozone, carbon dioxide, and hypochlorite. In at least one embodiment the BDD products are used to destroy biological contaminants in at least one portion of the apparatus.

In at least one embodiment the apparatus provides information to a control system such as that described in U.S. patent application Ser. No. 12/263904. In at least one embodiment the determined parameter readings are interfaced with a control system and they result in: the adding of more, adding of less, or altogether stopping to add: acid, base, caustic, corrosion inhibiter, neutralizer, film inhibiter, water, and any combination thereof. In at least one embodiment the sample is derived from boot waters.

In at least one embodiment the apparatus is used to measure properties of liquid samples different from and other than boot water samples.

In at least one embodiment iron levels in the sample are measured as follows: The reagent and a liquid sample react for a period of time before the absorbance is read as so the insoluble iron becomes solubilized and complexed. In at least one embodiment the time interval is at least 2 minutes. As normal, the first four blank sample points are read and stored as baseline readings for correcting the final absorbances for tube fouling. After reagent injection, the reacted sample is pumped for a certain amount of time, 7 seconds, to put the peak of the sample in the optical path of the colorimeter. After two minutes, a number of readings are taken (such as 20) and the results averaged.

Figure 9:
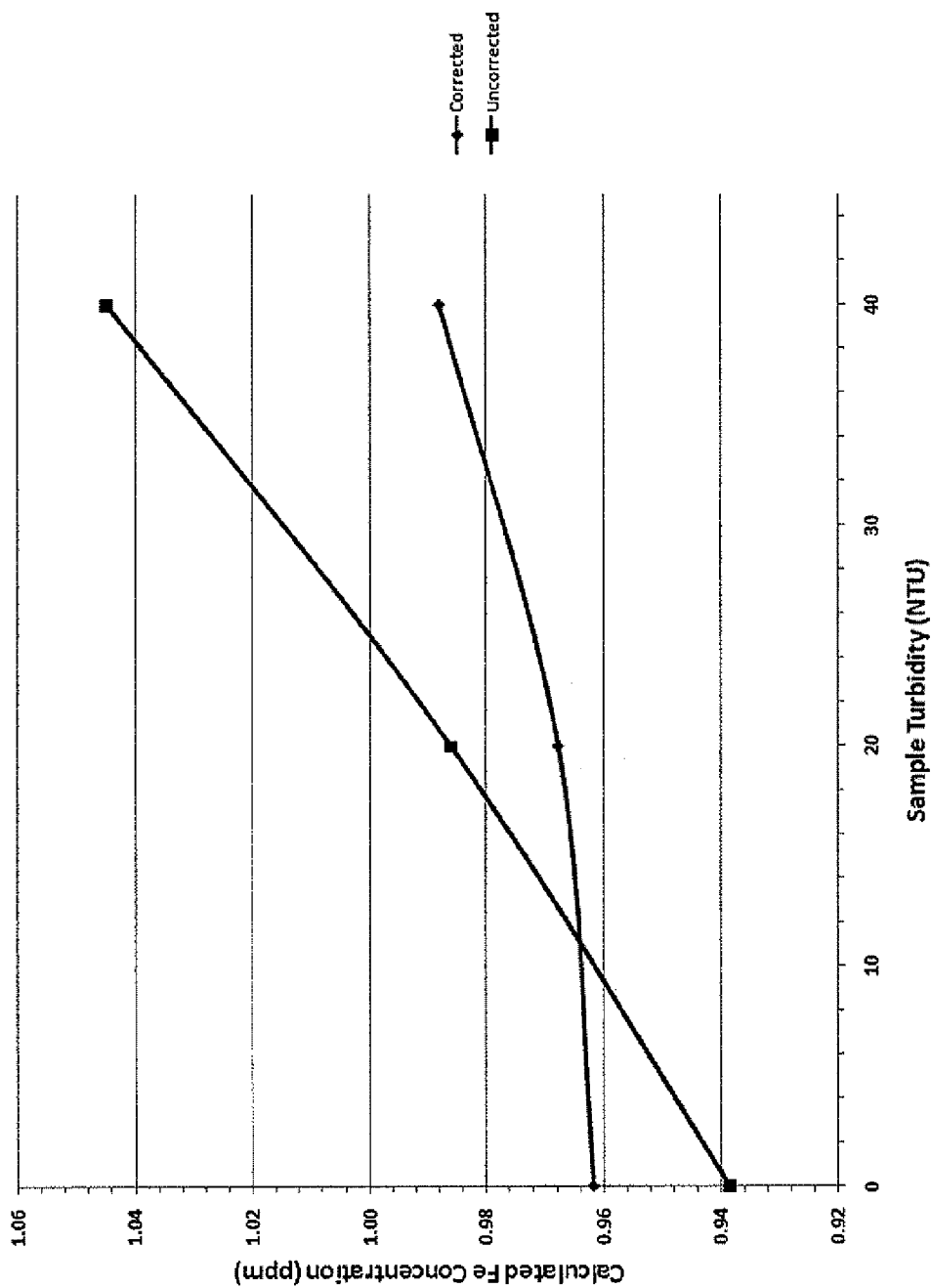
FIG. 9 is a graph used to illustrate turbidity correction in Fe measurements.

For each wavelength, the pure sample blank readings are subtracted from those taken after two minutes. Then the corrected absorbance at 690 nm is subtracted from those at 560 nm. The resulting value is put into a simple calibration equation of the form [Fe]=k×Abs, where Abs is the final corrected absorbance. The advantage of the 690 nm blanking step can be appreciated by referring to FIG. 9 which shows results for samples in which turbidity was added.

The correction is an improvement over no correction. Another advantage is correction for changes in absorbance caused by the buffer such as solubilization of suspended material.

In at least one embodiment chloride is measured as follows: Lucigenin fluorescence in acid solution is quenched by anions such as $Cl^-$ and $HS^-$. It is the most sensitive indicator for chloride with a $K_{SV}$=390 $M^{-1}$. A linear response to chloride is obtained with $F^0/F-1$, where $F^0$ is the fluorescence intensity for no chloride and F is the measured fluorescence intensity of the sample containing chloride. The slope of the response is determined during a two-point calibration. For the analysis procedure, the sample is acidified and then sparged to remove interfering $H_2S$. Then lucigenin is added and the mixed sample flows through the fluorometer. The first four blank sample points are read as baseline absorbance and fluorescence.

Data arrays for all channels are collected as the mixed sample flows through the fluorometer. FIG. 5 shows plots of the response for 0 ppm and 150 ppm chloride. One fluorescence curve is seen to be quenched by a factor of 2 in the 150 ppm plot. The transmittance curve for lucigenin shows a peak where the fluorescence curve peaks and it is this point where chloride is calculated. Other points can also be used since the ratio corrects for reagent concentration. The corrected peak absorbance is calculated by subtracting the baseline absorbance from the peak. Similarly, the corrected fluorescence is found by subtracting the baseline fluorescence from the peak. The ratio of the two corrected values is used in the calibration equation to obtain the chloride concentration in the sample.

Figure 10:
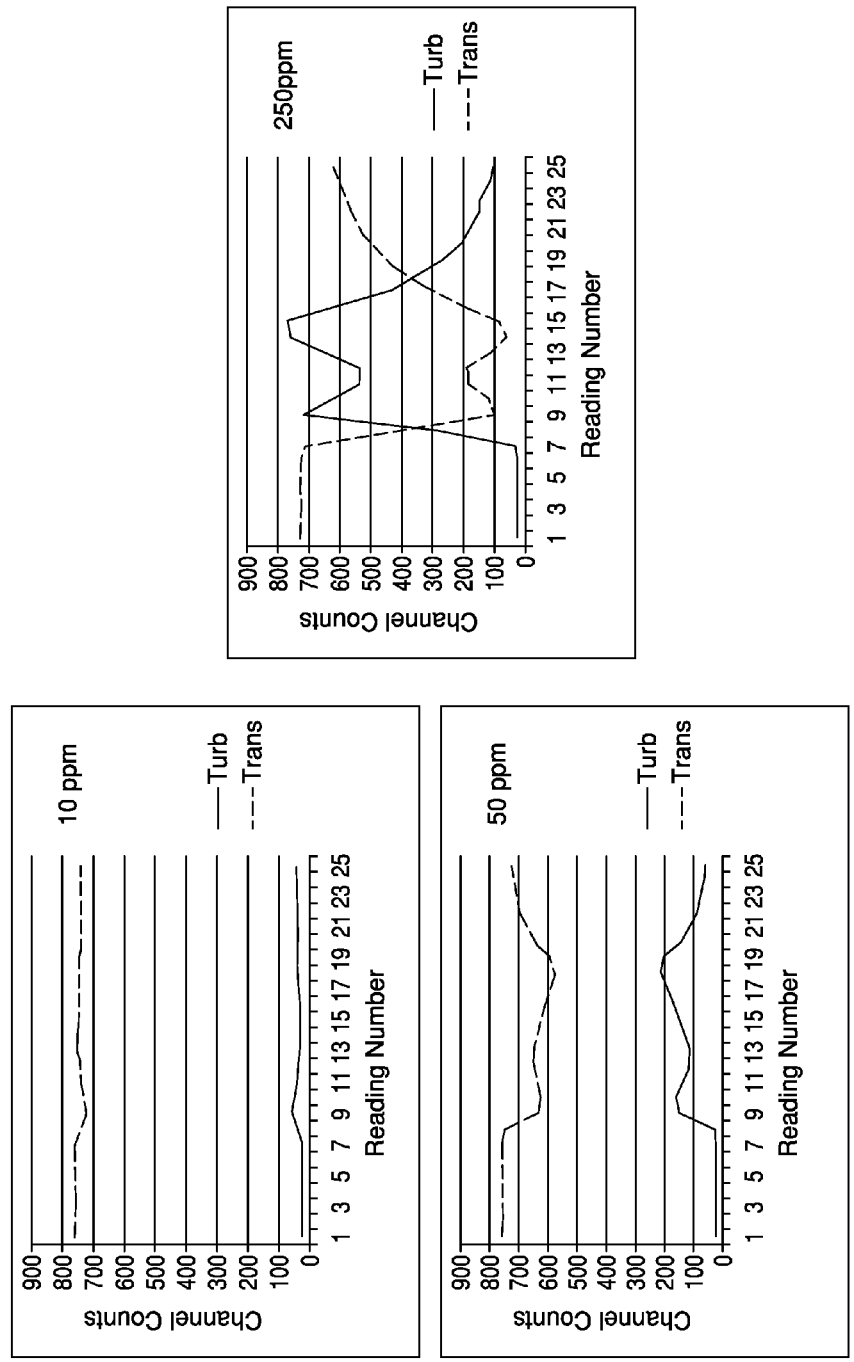
FIG. 10 is a graph illustrating response curves for chloride by turbidity using absorbance measurement. In this graph, Channel Counts is transmitted light intensity for the Trans curve. Absorbance of the suspended AgCl is calculated by log 10(ref/trans) where the reference curve is not shown. This absorbance is given as the X-axis in FIG. 11.
Figure 11:
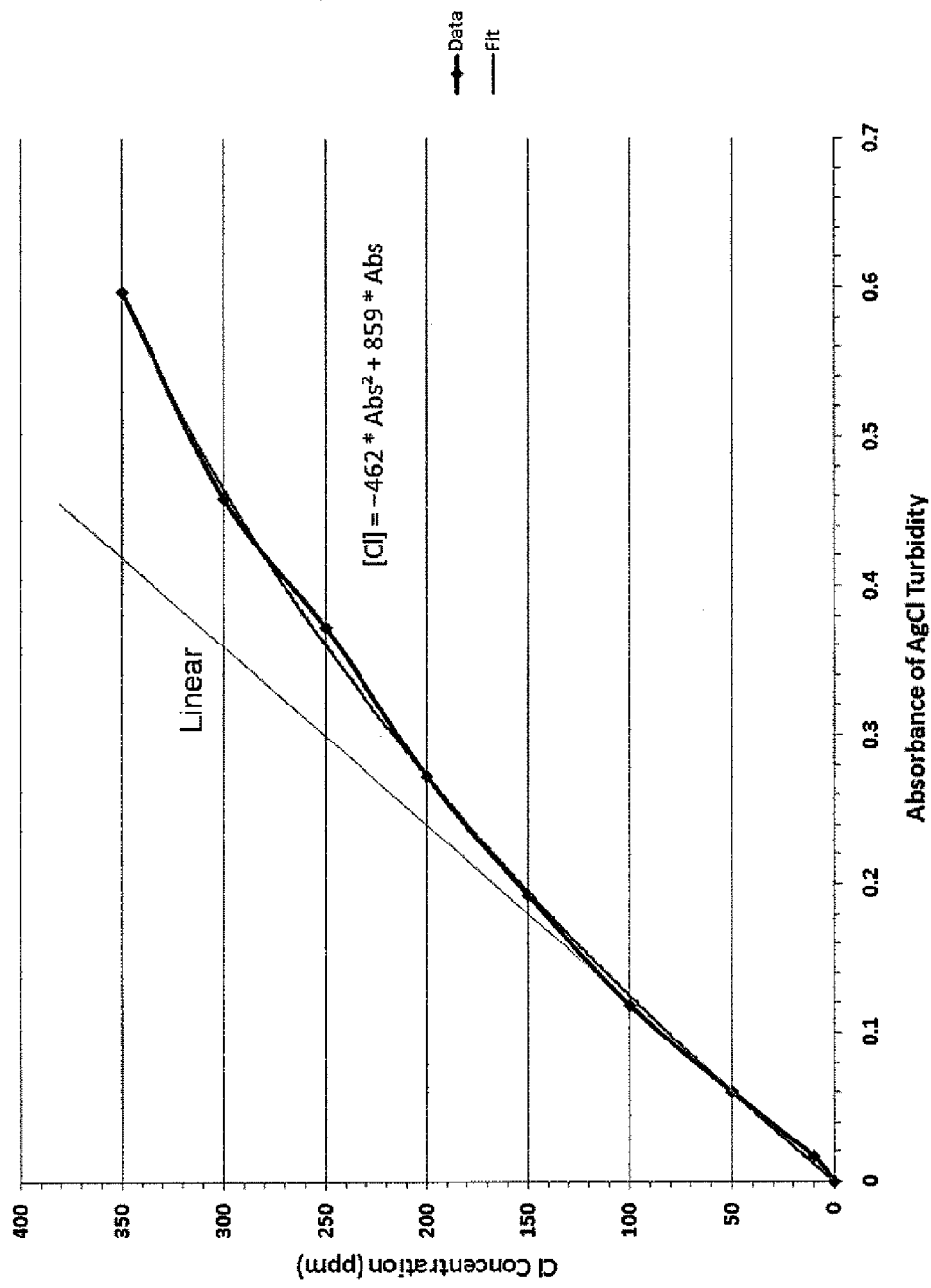
FIG. 11 is a graph illustrating a nonlinear calibration curve for chloride by absorbance of the turbidity formed by reaction of the sample with silver nitrate.

In at least one embodiment chloride is measured as follows: Reagent such as silver nitrate is added to a sample and the baseline absorbance values are obtained. The sample is read as it flows giving about 6-8 seconds for turbidity to form. FIG. 10 shows the turbidity and transmittance responses as the sample flows through the device. Quite different curves are seen depending on the chloride concentration. Doublet formation occurs above 10 ppm where the times of the peaks vary with concentration. This effect does not allow a static sample method to be used since the time when peaks elute is not known. (One embodiment here is that turbidity is measured at the peak of a flowing sample and not after a specified time since peak position will vary with chloride concentration.) The best results were obtained when the second transmittance peak is used. Baseline correction is applied to the peak absorbance from which the chloride concentration is derived. As seen in FIG. 11, the response is nonlinear and a polynomial of order 2 was fit to the data. Using standard equations, the coefficients for the $Abs^2$ and Abs terms are calculated during a three-point calibration. Optionally, at low chloride concentrations only the Abs term can be used as the response is nearly linear.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments described herein and incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method of measuring at least one property of a predominantly liquid sample, the method comprising the steps of:
positioning the sample within an apparatus, the apparatus comprising a boron doped diamond (BDD) cell, a chamber, and at least one reagent source constructed and arranged to feed at least one chemical reagent into the chamber,
pre-conditioning the sample by performing one or more pre-conditioning steps which include passing the sample through the BDD cell thereby oxidizing sulfoxy compounds within the sample via the BDD cell,
after pre-conditioning, adding the at least one chemical reagent to the sample in the chamber, the at least one chemical reagent capable of inducing a measurable optical effect when added to the sample that is directly related to the at least one property,
mixing the at least one chemical reagent with the sample in the chamber to form a mixture,
moving the mixture past an optical sensor,
measuring at least two optical properties of the mixture to determine a measured optical effect of the sample, and
deducing the value of the at least one property by comparing the measured optical effect to predetermined values associated with the at least one property,
wherein the measured optical effect is independent of the volume of the sample and independent of the volume of the at least one chemical reagent added to the sample.

2. The method of claim 1 wherein the at least one property is one item selected from the list consisting of: pH, iron concentration, chloride concentration, and any combination thereof.

3. The method of claim 1 wherein the at least two optical properties comprise at least one of a colorimetric effect, a turbidity effect, or a fluorescent effect.

4. The method of claim 1 wherein the measuring and analyzing the at least two optical properties of the predominantly liquid sample to determine the measured optical effect comprises (i) determining an absorbance level at a particular wavelength that is an isosbestic point for all values of the at least one property, and (ii) determining at least one other absorbance level for one other wavelength, and wherein the step of deducing the value of the at least one property comprises comparing the two absorbance levels with pre-determined data, and correlating the two absorbance levels to known absorbance levels of a particular value of the at least one property.

5. The method of claim 4, wherein determining the measured optical effect further comprises ratioing the absorbance levels determined at the isosbestic point and the one other wavelength, such that the measured optical effect comprises a ratio of the two absorbance levels.

6. The method of claim 1 wherein the measuring and analyzing the at least two optical properties of the sample to determine the measured optical effect comprises (i) determining a fluorescence level at a particular wavelength that is an isosbestic point for all values of the at least one property, and (ii) determining at least one other fluorescence level for one other wavelength, and wherein the step of deducing the value of the at least one property comprises correlating a ratio of the two fluorescence levels to a known ratio of fluorescence levels of a particular value of the at least one property.

7. The method of claim 1 wherein the measuring and analyzing the at least two optical properties of the sample to determine the measured optical effect comprises (i) determining an absorbance level at a particular wavelength that is an isosbestic point for all values of the at least one property, and (ii) determining a fluorescence level for one other wavelength, and wherein the step of deducing the value of the at least one property comprises correlating a ratio of the absorbance level and the fluorescence level to a control ratio of a known value of the at least one property.

8. The method of claim 1, wherein the apparatus further comprises a light source.

9. The method of claim 1, wherein the apparatus further comprises a light source positioned in line or perpendicular to the optical sensor.

10. The method of claim 9 in which the apparatus comprises at least two light sources and corresponding optical sensors in line with the light sources, a path between the light sources and corresponding optical sensors being substantially perpendicular to a flow path of the mixture, each of the optical sensors being constructed and arranged to measure an optical property of the same volume of the mixture in the same region of the flow path as the other optical sensors, and wherein the method further comprises:
turning on the at least two light sources, and
taking readings from the corresponding optical sensors.

11. The method in claim 10 wherein the turning on the at least two light sources and the taking readings from the corresponding optical sensors are performed simultaneously.

12. The method of claim 1, wherein the apparatus further comprises a vertically angled sensor flow path through which the mixture flows, and wherein the measuring of the at least two optical properties comprises light passing to the optical sensor passing horizontally through the mixture.

13. The method of claim 12, wherein the apparatus further comprises a tube downstream from the sensor, at least a portion of the tube is higher than the sensor and extends at an more horizontal angle than the vertically angled sensor flow path, the tube is constructed and arranged to facilitate the migration of gas bubbles away from the sensor, wherein the tube is in one shape selected from the list consisting of: inverted U-shaped, bent, curved, and angled.

14. The method of claim 1 where temperature measurements are taken to correct for temperature effects.

15. The method of claim 1,
wherein the apparatus further comprises a gas source,
the step of pre-conditioning the sample further comprises adding a pre-sparge material to the sample and then sparging the sample at the gas source upstream from the sensor, wherein the adding a pre-sparge material to the sample comprises adding at least one item selected from the list consisting of: acid, hydrogen peroxide, and any combination thereof, such that the pre-sparge material increases the rate of expulsion of undesired materials from the sample.

16. The method of claim 1, in which the apparatus is interfaced with a control system governing at least some of the operations of a chemical process stream from which the sample was taken, the deduced value of the at least one property resulting in the control system implementing a counter-measure in response to the at least one property.

17. The method of claim 1 wherein the at least one chemical reagent is selected from the list consisting of: bromcresol purple, fluorescein, pyrenetetrasulfonic acid (PTSA), 5,10,15,20-tetraphenyl-21H,23H-porphine-tetrasulfonic acid, tetrasodium hydrate (TPPTSA), calcein blue, Ferrozine, silver nitrate, thioglycolic acid, ammonia, pH buffer, ferric iron reductant, fluorescent dye, lucigenin, and any combination thereof.

18. The method of claim 1 further comprising the step of adding a foulant removing cleaner to at least one item used to measure a property of the sample, the cleaner being one item selected from the list consisting of: ethanolamine, methoxy propylamine, ammonium hydroxide, hypochlorite, hydrogen peroxide, nitric acid, and any combination thereof.

* * * * *